United States Patent
Ganzoni et al.

(10) Patent No.: US 8,051,498 B2
(45) Date of Patent: Nov. 8, 2011

(54) RETENTION GARMENT OR UNDERGARMENT

(75) Inventors: Stefan Ganzoni, Bottmingen (CH); Bertrand Lun, Saint-Etienne (FR)

(73) Assignee: GSl Holding (SA), Saint-Louis (FR)

(*) Notice: Subject to any disclaimer, the term of this patent is extended or adjusted under 35 U.S.C. 154(b) by 1301 days.

(21) Appl. No.: 10/552,700

(22) PCT Filed: Apr. 7, 2004

(86) PCT No.: PCT/FR2004/000865
§ 371 (c)(1),
(2), (4) Date: Jun. 7, 2006

(87) PCT Pub. No.: WO2004/092611
PCT Pub. Date: Oct. 28, 2004

(65) Prior Publication Data
US 2007/0000027 A1    Jan. 4, 2007

(30) Foreign Application Priority Data
Apr. 11, 2003  (FR) ..................................... 03 04565

(51) Int. Cl.
*A41B 11/00*   (2006.01)
(52) U.S. Cl. ........ 2/239; 2/240; 2/241; 2/242; 66/178 R
(58) Field of Classification Search .............. 2/239, 240, 2/241, 242; 66/178 R
See application file for complete search history.

(56) References Cited

U.S. PATENT DOCUMENTS

| | | | | | |
|---|---|---|---|---|---|
| 1,708,342 | A | * | 4/1929 | Vogt | 66/186 |
| 1,724,784 | A | * | 8/1929 | Teichmann | 2/239 |
| 1,898,001 | A | * | 2/1933 | Carmer | 66/172 R |
| 4,172,456 | A | * | 10/1979 | Zens | 602/63 |
| 4,571,960 | A | | 2/1986 | Anthony et al. | |
| 5,005,567 | A | | 4/1991 | Gilman et al. | |
| 5,412,957 | A | | 5/1995 | Bradberry et al. | |
| 5,417,091 | A | * | 5/1995 | Moser | 66/178 R |
| 6,371,933 | B1 | * | 4/2002 | Gardon-Mollard | 602/62 |
| 6,523,729 | B1 | | 2/2003 | Gardon-Mollard | |

FOREIGN PATENT DOCUMENTS
WO    01/00118    1/2001

* cited by examiner

*Primary Examiner* — Khoa Huynh
*Assistant Examiner* — Alissa Tompkins
(74) *Attorney, Agent, or Firm* — Young & Thompson

(57) ABSTRACT

The invention relates to the domain of retention garments and to those used to facilitate the application of the same. The invention especially relates to a garment or an undergarment to be placed under a retention garment, which is characterized in that it is essentially knitted with at least two different stitch structures, a first, knitted according to a float stitch pattern in a textile material having a smooth outer surface, and a second, knitted according to a weft stitch pattern in an adapted elastic textile material having a weft count of between 240 dtex and 600 dtex, in such a way as to generate a slight compression or retention.

14 Claims, 2 Drawing Sheets

RETENTION GARMENT OR UNDERGARMENT

BACKGROUND OF THE INVENTION

This invention relates to treatments of venous pathology, more exactly those implementing so-called support or compression articles, and more particularly the field of producing articles derived from genuine support or compression articles as such, especially the production of "under-articles" such as understockings for support articles.

Support articles in the sense of this description are defined as all tubular compressive ortheses made of a knit, elastic textile material, except for bandages, and more especially compressive ortheses of one or two lower limbs. The support "under-articles" for the purposes of this invention are articles (typically socks, stockings, knee socks, tights, and the like) designed to be slipped on first and thus to be in direct contact with the skin of the patient. Such articles are designed first of all to improve the comfort of the wearer's skin, but can equally advantageously exhibit different properties intended, for example, to yield light support or to reinforce the support action of the main article. In any case, the main innovation of the aforementioned articles resides in the fact that they can both be more easily slipped on by the user and can provide increased comfort.

Actually, placing support articles typically of a high class, typically of class 3 (strong compression between 27 and 48 hPa) or of class 4 (extra-strong compression greater than 48 hPa), on the limbs to be treated still today comprises a genuine everyday problem that confronts patients and/or caregivers.

This problem is the more critical in that correct and consistent placement is essential to optimize adherence to the treatment prescribed by the physician and thus its chances of success.

The problems associated with placement are inherent in the enhanced support material or textile material and can even, if necessary, be exacerbated by a diminished physical state of the patient, in particular when the latter must apply said treatment himself.

Numerous types of mechanical devices for slipping on articles are already known, in particular in the form of accessories generally for stockings, that are for the most part heavy metallic structures that are difficult to manipulate. These devices are not satisfactory, however, the residual efforts to be supplied by the patient and the complexity of their use still being too weighty and thus discouraging.

There is thus a real need for a simple and economical article that significantly facilitates the placement of the aforementioned support articles.

There are, moreover, support articles that can be used alone (for light support) or in combination with a support article of a high class in order, moreover, to reinforce already existing properties of the primary support article. However, the act of slipping a standard support article over another still entails major difficulties today.

SUMMARY OF THE INVENTION

The object of this invention is to alleviate the aforementioned problems and to provide such articles.

To do this, the object of the invention is a support article or under-article that can be used alone or preferably under a support article while in direct contact with the skin of the wearer, characterized in that it is essentially knit with at least two different mesh structures, i.e.:

a first structure for a first zone of said article or under-article that extends from the first end intended for the toes to the level of the ankle bones of said wearer, this zone being knitted according to a so-called "floating mesh" pattern in a textile material with an outer surface that is opposite the one in contact with the skin of said wearer and that is smooth, a second structure for a second zone of said article or under-article that extends from the aforementioned ankle bones to the second or other end opposite that intended for said toes, this zone being knitted according to a so-called "woven mesh" pattern, in an adapted elastic textile material with a weave titer of between 240 dtex and 600 dtex in such a way as to afford light compression or support at the level of said second zone.

Such an "under-article" can be an article placed, for example, under a stocking in the strict sense (covering the thigh and the hollow of the knee), under tights (covering the two lower limbs and the abdomen up to the waist, in a single piece), under a single legging (legging provided with a single leg, designed to support one of the lower limbs), or else under a sock (covering the hollow of the knee alone).

The invention will be better understood by way of the following description that relates to preferred embodiments given by way of nonlimiting examples, and explained with reference to the attached schematic drawing in which the sole figure is a standardized representation of the floating mesh used to produce a support article or under-article according to the invention.

According to this invention, the support article or under-article that can be used alone or preferably under a support article by being in direct contact with the skin of the wearer is characterized in that it is essentially knit with at least two different mesh structures, i.e.:

a first structure for a first zone of said under-article that extends from the end intended for the toes to the level of the ankle bones of said wearer, this zone being knitted according to a so-called "floating mesh" pattern in a textile material with an outer surface that is opposite that in contact with the skin of said wearer and that is smooth, a second structure for a second zone of said under-article that extends from the aforementioned ankle bones to the other end opposite that intended for said toes, this zone being knitted according to a so-called "woven mesh" pattern, in an adapted elastic textile material with a weave titer of between 240 dtex and 600 dtex in such a way as to afford light compression or support at the level of said second zone.

DESCRIPTION OF PREFERRED EMBODIMENTS

Figure 1:
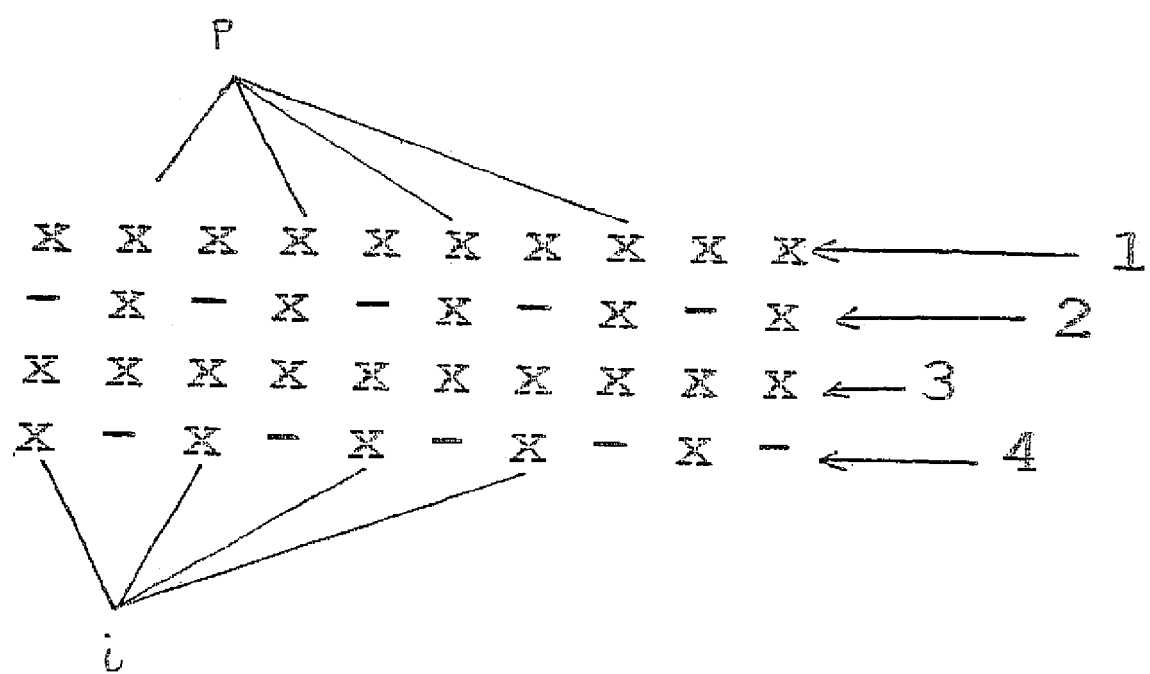
FIG. 1 is schematic diagram of an embodiment of the present invention.
Figure 2:
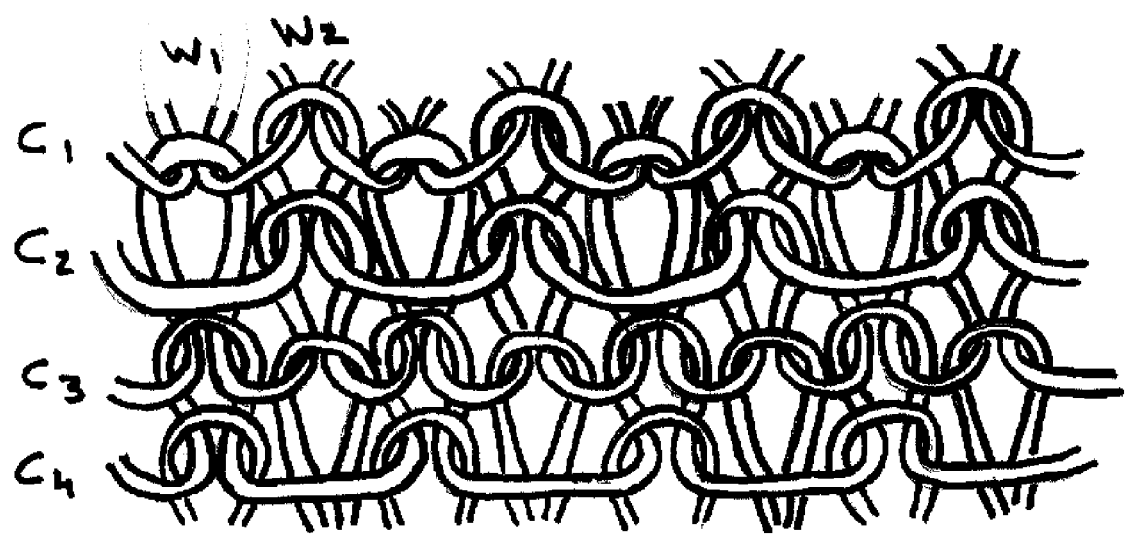
FIG. 2 is a pictorial representation of the embodiment of FIG. 1.

As shown in FIGS. 1 and 2, the so-called "floating mesh" mesh has a particular knit structure that makes it possible to obtain, for example with a flat synthetic filament, a smoother outer surface. The basic pattern defining completely said floating mesh is obtained on four rows of mesh:

the first row (1) is composed of meshes labelled "X" whose loops are completely formed on all of the columns, the second row (2) is composed of meshes whose loops are completely formed on even columns (p) and whose loops are not formed at all on odd columns (i), the unformed loops being symbolized by a "-", the third row (3) is again composed of meshes whose loops are completely formed on all of the columns, and the fourth row (4) is composed of meshes whose loops are completely formed on odd columns and whose loops are not formed at all on even columns.

In FIG. 2, the pattern of FIG. 1 is repeated with the courses marked $C_1, \ldots C_4$ and the wales marked $W_1, W_2$.

Advantageously, the article or under-article according to this invention is characterized in that the smooth textile material used for the first structure is a synthetic textile material, preferably a flat synthetic filament, untextured and preferably in combination with an elastothane (elastomer fiber with high elasticity marketed especially under the trademark name Lycra).

In this way, it can be ensured that the side that will be in contact with the support article as such will allow facilitated sliding (very low coefficient of friction) and thus greater ease of slipping the latter over said under-article.

Preferably the article or under-article according to the invention is characterized in that the smooth textile material used for the first structure is a polyamide in the form of a filament.

For this reason, all of the polyamides ordinarily used in the field of textiles can be used for the production of the article or under-article according to the invention. By way of indication, a lighter nylon, of the nylon 6.6 type or the like, is preferred for use.

According to another advantageous characteristic, the textile material used for the second structure comprises at most 50% by weight of a natural textile material, such as cotton, linen, or silk.

Thus, it becomes possible to increase the overall comfort of said article or under-article, especially by increasing the ventilation of the foot in this zone and thus reducing the problems associated with perspiration.

Advantageously, the material used for the second structure is a modified synthetic textile material (for example modified chemically by grafting the desired functional groupings onto the base skeleton of the polymer or copolymer comprising said synthetic textile material) with a physico-chemical property that has been improved relative to the base synthetic textile material, such as improved thermal insulation, water vapor permeability, bactericidal and/or fungicidal action, an odor-suppression effect, etc.

Thus, it becomes possible to impart an additional functionality to the object of this invention and to suggest a product that is more or less customized depending on the wishes of the patient and the recommendations of the treating physician.

According to another advantageous characteristic, the article or under-article according to the invention is also characterized in that it comprises a so-called alternative knitted heel with a flat synthetic filament.

Such a heel, well known in the field of textile manufacture, is preferably knitted with a flat synthetic filament. In particular, it has the advantage of also increasing comfort for the wearer.

Alternatively, and according to another advantageous characteristic, the article or under-article according to the invention is, moreover, characterized in that it comprises a zone of wider cross-section at the level of the ankle. Thus, it relatively economically compensates for the loss of comfort induced by the absence of the alternative heel.

Preferably, the compression or support applied by the article or under-article according to this invention to the wearer at the level of said first zone is less than 13 hPa.

Even weak support is designed above all to facilitate the garment's being slipped on while ensuring that it is kept adequately in place, and does not have, in contrast to the second zone, as a first function to ensure a therapeutic effect at the level of the foot, even if such an effect can optionally be exploited in certain cases.

Advantageously, the article or under-article according to the invention is also characterized in that the compression or support applied to the wearer at the level of said second zone is between 13 and 30 hPa, preferably between 20 and 30 hPa.

This more moderate compression may be sufficient in less serious pathological cases in which products of higher classes are not necessary.

Of course, this perfectly managed support can be arithmetically added to the support or compression provided by the genuine support article, for example by a support stocking, in particular a support stocking of a clearly higher class.

More specifically, the article or under-article according to this invention is characterized in that it is a stocking or an understocking, tights or undertights, a legging or an underlegging, i.e., an article placed under a legging provided with a single leg intended to support a single lower limb, or a sock or an undersock.

The operation of the under-article according to the invention is very simple and greatly facilitates placement on said under-article of other support products that are much more difficult to slip on by themselves. In fact, it is sufficient to place (slip on) the under-article adapted to the desired effect in the conventional manner. Due to its light support and its specific structure, no special effort is necessary for this purpose, and this operation can be carried out by most patients. Finally, it is sufficient to normally slip on the support article as such; this is greatly facilitated by the smooth surface of the under-article already in place.

Based on the products and processes according to the invention, the therapeutic application of support products (in particular of a high or very high class) can be done without undue effort, in an exact and reproducible manner in order to minimize the constraints that develop as well as their adverse effects (strenuous efforts to be applied, placement errors, random adherence or non-adherence to the prescribed treatment . . . ) and to guarantee to the patient effective medical treatment according to the prescription of the physician.

The object of this invention is also a process for placement of a support article, characterized in that it consists essentially in placement of an under-article according to the invention on the part of the body to be treated prior to placement of said support article.

In this way, the placement of support articles, especially the placement of those of a high class, is facilitated, and, if necessary, additional functionalities can be provided to the patient.

Of course, the invention is not limited to the described embodiments and to the attached drawing. Modifications remain possible, especially from the standpoint of the composition of the various components or by substitution of technical equivalents, without thereby exceeding the scope of protection of the invention.

The invention claimed is:

1. A fabric for a garment, comprising:
a first structure for a first zone of the garment that extends from a first end intended for toes of a wearer to a level of ankle bones of the wearer, the first structure being a knitted floating mesh pattern in a textile material with an outer surface that is opposite that in contact with skin of the wearer and that is smooth; and a second structure for a second zone of the garment that extends from the aforementioned ankle bones to a distal second end opposite the first end, the second structure being a knitted woven mesh pattern, in an adapted elastic textile material with a weave titer of between 240 dtex and 600 dtex in such a way as to afford compression or support in the second zone greater than in the first zone, wherein the floating mesh pattern includes four courses of mesh sequentially arranged with a first of the courses comprising meshes whose loops are completely formed on all wales of the pattern, a second of the courses comprising meshes whose loops are completely formed on even wales and whose loops are not formed at all on odd wales, a third of the courses comprising meshes whose loops are completely formed on all wales of the pattern, and a fourth of the courses comprising meshes whose loops are completely formed on odd wales and whose loops are not formed at all on even wales.

2. The fabric according to claim 1, wherein the smooth textile material used for the first structure is a synthetic textile material with a flat synthetic filament, untextured and in combination with an elastothane.

3. The fabric according to claim 1, wherein the smooth textile material used for the first structure is a polyamide in the form of a filament.

4. The fabric according to claim 1, wherein the textile material used for the second structure comprises at most 50% by weight of a natural textile material.

5. The fabric according to claim 1, wherein the textile material used for the first and/or second structure comprises a synthetic textile material with an improved physico-chemical property.

6. The fabric according to claim 1, further comprising an alternative knitted heel with a flat synthetic filament.

7. The fabric according to claim 1, wherein the compression or support applied to the wearer at the level of the first zone is less than 13 hPa.

8. The fabric according to claim 1, wherein the compression or support applied to the wearer at the level of the second zone is between 13 and 30 hPa.

9. The fabric according to claim 1, wherein the fabric is part of a stocking or an under-stocking.

10. The fabric according to claim 1, wherein the fabric is part of tights or undertights.

11. The fabric according to claim 1, wherein the fabric is part of legging or an underlegging.

12. The fabric according to claim 1, wherein the fabric is part of a sock or an undersock.

13. A fabric for a garment, comprising:

a first structure for a first zone of the garment that extends from a first end intended for toes of a wearer to a level of ankle bones of the wearer, the first structure being a knitted floating mesh pattern in a textile material with an outer surface that is opposite that in contact with skin of the wearer and that is smooth, the floating mesh pattern providing a compression to the wearer in the first zone less than 13 hPa; and a second structure for a second zone of the garment that extends from the ankle bones to a second distal end opposite the first end, the second structure being a knitted woven mesh pattern in an adapted elastic textile material with a weave titer of between 240 dtex and 600 dtex, the knitted woven mesh pattern providing a compression in the second zone between 13 and 30 hPa, wherein the floating mesh pattern includes four courses of mesh sequentially arranged with a first of the courses comprising meshes whose loops are completely formed on all wales of the pattern, a second of the courses comprising meshes whose loops are completely formed on even wales and whose loops are not formed at all on odd wales, a third of the courses comprising meshes whose loops are completely formed on all wales of the pattern, and a fourth of the courses comprising meshes whose loops are completely formed on odd wales and whose loops are not formed at all on even wales.

14. An undergarment comprising the fabric of claim 13.

* * * * *